(12) United States Patent
Nakakado

(10) Patent No.: US 7,449,084 B2
(45) Date of Patent: Nov. 11, 2008

(54) WEB WELDING SYSTEM

(75) Inventor: Masaki Nakakado, Osaka (JP)

(73) Assignee: ZUIKO Corporation, Osaka (JP)

( * ) Notice: Subject to any disclaimer, the term of this patent is extended or adjusted under 35 U.S.C. 154(b) by 348 days.

(21) Appl. No.: 10/597,489

(22) PCT Filed: Jan. 11, 2005

(86) PCT No.: PCT/JP2005/000164

§ 371 (c)(1),
(2), (4) Date: Jul. 27, 2006

(87) PCT Pub. No.: WO2005/080065

PCT Pub. Date: Sep. 1, 2005

(65) Prior Publication Data

US 2008/0236756 A1    Oct. 2, 2008

(30) Foreign Application Priority Data

Feb. 25, 2004   (JP) .............................. 2004-048912

(51) Int. Cl.
*B32B 37/00* (2006.01)

(52) U.S. Cl. .................................. 156/580.1; 156/73.1

(58) Field of Classification Search .................. 156/64, 156/73.1, 359, 361, 555, 580.1, 580.2, 582
See application file for complete search history.

(56) References Cited

U.S. PATENT DOCUMENTS 4,430,148 A    2/1984  Schaefer 4,713,132 A * 12/1987  Abel et al. .................. 156/73.1
5,660,679 A *  8/1997  Rajala et al. .............. 156/580.1
5,817,199 A   10/1998  Brennecke et al.
2007/0251643 A1* 11/2007  Umebayashi et al. ....... 156/350

FOREIGN PATENT DOCUMENTS

| EP | 0 092 866 | 11/1983 |
| JP | 42-21754 | 12/1967 |
| JP | 06-155577 | 6/1994 |
| JP | 2001-506945 | 5/2001 |
| JP | 2001-151208 | 6/2001 |
| JP | 2004-330622 | 11/2004 |
| WO | 98/28123 | 7/1998 |

OTHER PUBLICATIONS

International Search Report for corresponding Application No. PCT/JP2005/000164 mailed Apr. 12, 2005.

* cited by examiner

*Primary Examiner*—James Sells
(74) *Attorney, Agent, or Firm*—Renner, Otto, Boiselle & Sklar, LLP

(57) ABSTRACT

An object of the present invention is to provide a welding system wherein the positional accuracy of welding and the quality of welding are improved. The present welding system includes an ultrasonic welder for welding a plurality of webs W together while carrying the webs W. The ultrasonic welder includes: an anvil roller 10 including a pair of anvils 11, 12; a first ultrasonic horn 21 and a second ultrasonic horn 22 that apply vibration energy to the webs W in cooperation with the pair of anvils 11, 12. The pair of anvils 11, 12 are provided symmetrically with each other with respect to an axis line O of the anvils roller 10. The first and second ultrasonic horns 21, 22 apply the vibration energy to the webs W simultaneously while each of the anvils 11, 12 faces the first or second ultrasonic horn 21, 22.

12 Claims, 6 Drawing Sheets

WEB WELDING SYSTEM

TECHNICAL FIELD

The present invention relates to a welding system for welding a plurality of webs, which is sometimes referred to as "sealing".

BACKGROUND ART

Hitherto, a welding system wherein a plurality of ultrasonic horns are provided around one anvil roller is known (for example, the following first patent document).

The first patent document: Japanese Laid-Open Patent Publication No. 2004-330622 (abstract)

DISCLOSURE OF THE INVENTION

However, in such a conventional welding system, since a plurality of ultrasonic horns are provided around one anvil roller, the anvil roller is subject to large loads caused by ultrasonic vibration energy. Thus, the durability of the anvil roller may be impaired. Further, when the ultrasonic horns apply ultrasonic vibration simultaneously to the webs to weld the webs, the vibration causes positional displacement of the anvil roller. Accordingly, positional accuracy of welding may be decreased or quality of welding may be decreased.

An object of the present invention is to provide a new welding system wherein the positional accuracy of welding and the quality of welding are improved and the durability of the anvil roller is enhanced.

In order to achieve the object, a welding system of the present invention includes an ultrasonic welder for welding a plurality of webs together while carrying the webs.

The ultrasonic welder comprises an anvil roller including a pair of anvils and a first ultrasonic horn (vibrating body) and a second ultrasonic horn (vibrating body) that apply vibration energy to the webs in cooperation with the pair of anvils. The pair of anvils are provided symmetrically with each other with respect to an axis line of the anvils roller.

The first and second ultrasonic horns are arranged so that one anvil of the pair can face the first ultrasonic horn at the same time as the other anvil of the pair faces the second ultrasonic horn.

This system includes carrying means for carrying the webs so that the webs pass a first gap between the anvil roller and the first ultrasonic horn and then pass a second gap between the anvil roller and the second ultrasonic horn.

The first and second ultrasonic horns apply the vibration energy to the webs simultaneously while each of the anvils faces the first or second ultrasonic horn.

In this system, the welding of the webs is performed simultaneously at two locations. At this time, two opposite forces from the ultrasonic horns approximately toward the center of the anvil roller are applied simultaneously to the anvil roller via the webs.

Since the anvil roller receives simultaneously the two forces that are in opposite directions to each other, shock loads applied to the anvil roller due to the ultrasonic vibration energy is decreased, which makes the anvil roller less readily displace even when the ultrasonic horns applies the vibration energy to the anvil roller. Accordingly, the positional accuracy of the welding is improved.

According to a preferred aspect of the present invention, the welding system further comprises a velocity-changing device for increasing and decreasing a moving velocity of the webs.

By the velocity-changing device, the moving velocity of the webs at the first and second gaps when the first and second ultrasonic horns apply the vibration energy to the webs is set smaller than that at a position where the webs enter into the velocity changing device and/or that at a position where the webs exit from the velocity-changing device.

In this aspect, since the webs have longer time to receive the vibration energy, the quantity of the received vibration energy per unit area of the webs is increased. Accordingly, the reliability of the welding can be enhanced.

Furthermore, since the two ultrasonic horns are actuated simultaneously, the number of times the velocity-changing device changes the moving velocity of the webs can be decreased, and so, the number of times a prime mover (servo motor) of the velocity-changing device is subject to loads caused at the time of changing the moving velocity and the number of times dancer rollers of the velocity-changing device are moved can be halved. Accordingly, the durability of the device is enhanced.

In this aspect, the velocity-changing device may comprises: a first dancer roller that receives the webs flowing from an upstream side and releases the webs toward the first gap; a second dancer roller that receives the webs released from the second gap and releases the webs toward a downstream side; and moving means for moving the first and second dancer rollers. In this structure, the moving means may move the first roller and the second roller in generally opposite directions with each other so that the moving velocity of the webs is increased and decreased.

According to another preferred aspect of the present invention, the welding system further comprises a velocity-changing device for increasing and decreasing a moving velocity of the webs. The velocity-changing device comprises: a first dancer roller that receives the webs flowing from an upstream side and releases the webs toward the first gap; a second dancer roller that receives the webs released from the second gap and releases the webs toward a downstream side; moving means for moving the first and second dancer rollers; and a first driving means for rotatably driving the first and second dancer rollers.

In this aspect, a distance between the first and second dancer rollers may be substantially equal to or smaller than a diameter of the anvil roller.

If the distance between the two dancer rollers is large, the entire system including the velocity-changing device would be large in size. On the contrary, if, as mentioned above, the distance between the dancer rollers is approximately the same as or smaller than the diameter, the entire system becomes small in size.

It is preferred that the web welding system of this aspect further comprises a timing belt trained around a plurality of rollers including the first and second dancer rollers and a drive roller, for rotating the plurality of rollers in synchronism.

In this case, since the distance between the dancer rollers is small, the timing belt can be shortened. Accordingly, a commercially available timing belt becomes adoptable.

In addition, the web welding system may further comprise: a drive roller which the timing belt is trained about, the drive roller rotatably driven by the first driving means; a second driving means for rotatably driving the adjustment roller; and a control device. In this case, the control device controls the moving means, the first driving means and the second driving means so that both of a circumferential velocity of the adjustment roller and a circumferential velocity of the drive roller are equal to the moving velocity of the webs between the first and second dancer rollers.

According to another preferred aspect of the present invention, when each anvil of the pair faces the first ultrasonic horn or the second ultrasonic horn, the first and second ultrasonic horns are controlled to apply the vibration energy to the webs so that ultrasonic welding of the webs is performed. On the other hand, when the ultrasonic welding of the webs is not performed, the first and second ultrasonic horns are controlled not to apply the vibration energy to the webs.

In this aspect, since the horns need not be actuated continuously, electric power cost can be reduced. Furthermore, since the vibration energy is not applied to a portion of the webs which does not require the welding, the portion of the webs is unlikely to be creased.

According to another preferred aspect of the invention, the carrying means comprises: a adjustment roller that is rotatably supported; supporting means for rotatably supporting the adjustment roller selectively at a first position or a second position which is different from the first position. The webs flowing out of the first gap flow along an outer circumferential surface of the adjustment roller, and then are carried into the second gap.

When a semi-finished product including the webs is to be processed into a worn article of a first size, the adjustment roller is supported at the first position by the supporting means. On the other hand, when the semi-finished product including the webs is to be processed into a worn article of a second size that is different from the first size, the adjustment roller is supported at the second position by the supporting means.

The first and second ultrasonic horns weld a portion of the webs that is to be an end portion of an individual worn article, respectively, the length of the webs between the first gap and the second gap corresponds to the length of the product, i.e., the worn article, or a multiple thereof. Accordingly, the length of the produced worn article can be changed by means of changing the position where the adjustment roller is supported. That is, since the intervals of welded portions of the web can be adjusted by means of changing the position of the adjustment roller, one web welding system can produce worn articles of various sizes.

In this aspect, an angular velocity of the anvil roller may be controlled so that, according to the size of the worn article to be produced, one anvil of the pair can face the first ultrasonic horn at the first gap at the same time as the other anvil of the pair faces the second ultrasonic horn at the second position.

DESCRIPTION OF THE REFERENCE NUMERALS

Figure 1:
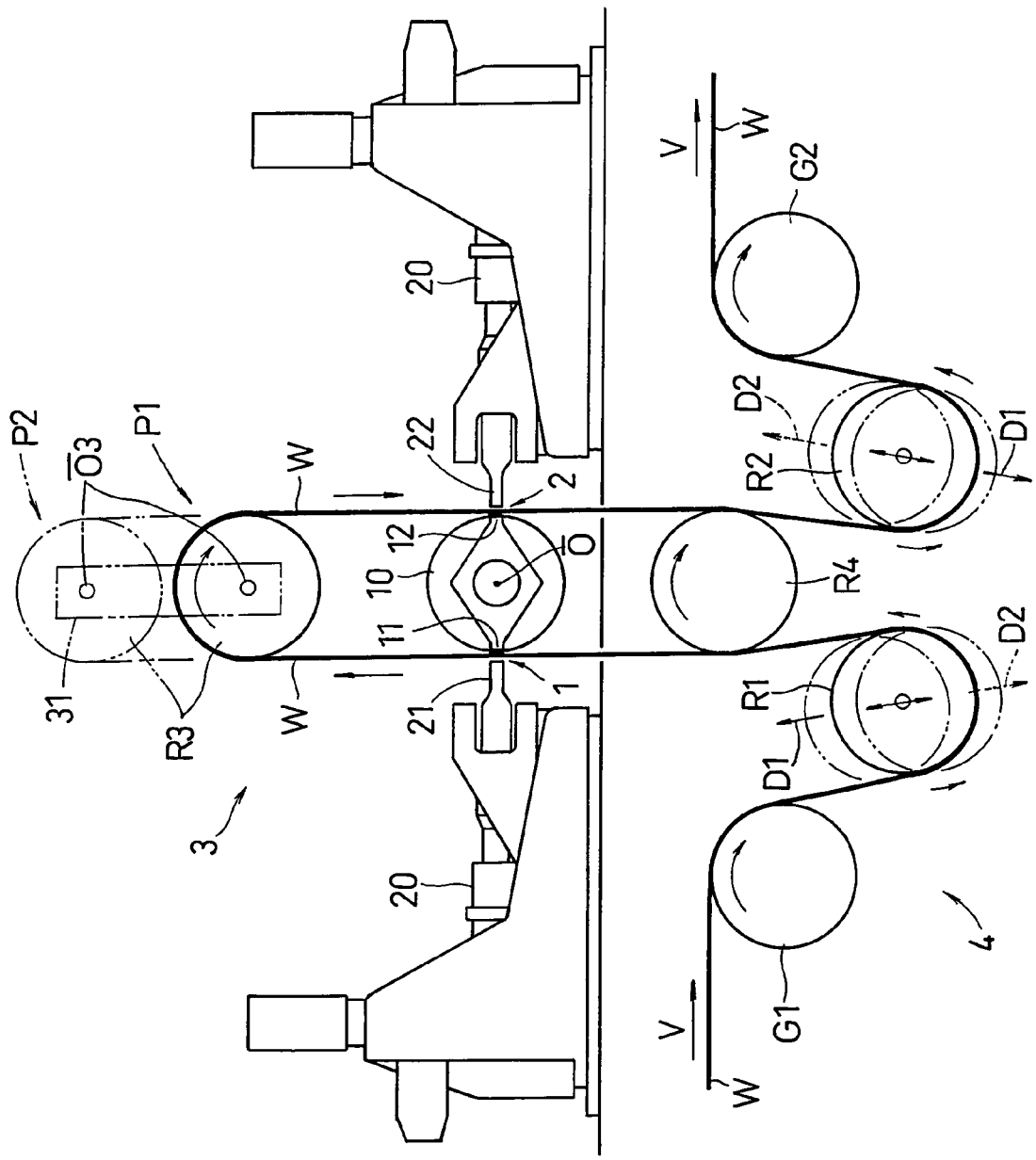
FIG. 1 is a schematic side view showing a welding system of the first embodiment.

1: First gap
2: Second gap
3: Carrying means
4: Velocity-changing device
5: Control device
10: Anvil roller
11, 12: Anvil
21: First ultrasonic horn
22: Second ultrasonic horn
31: Supporting means
32: Second driving means
40: Moving means
41: First driving means
P1: First position
P2: Second position
R1: First dancer roller
R2: Second dancer roller
R3: Adjustment roller
R4: Drive roller
TB: Timing belt
W: Web

BEST MODE FOR CARRYING OUT THE INVENTION

The present invention will be understood more clearly from the following description of preferred embodiments taken in conjunction with the accompanying drawings. However, it will be appreciated that the embodiments and the drawings are given for the purpose of mere illustration and explanation and that the scope of the present invention is to be defined by the appended claims. In the accompanying drawings, the same reference numerals denote the same or corresponding elements throughout several figures.

Embodiments of the present invention will now be described with reference to the drawings.

In the following description, an important part of a web welding system of the present invention will first be described in the first embodiment, and a velocity-changing device that is provided in the web welding system will then be described.

Figure 2A:
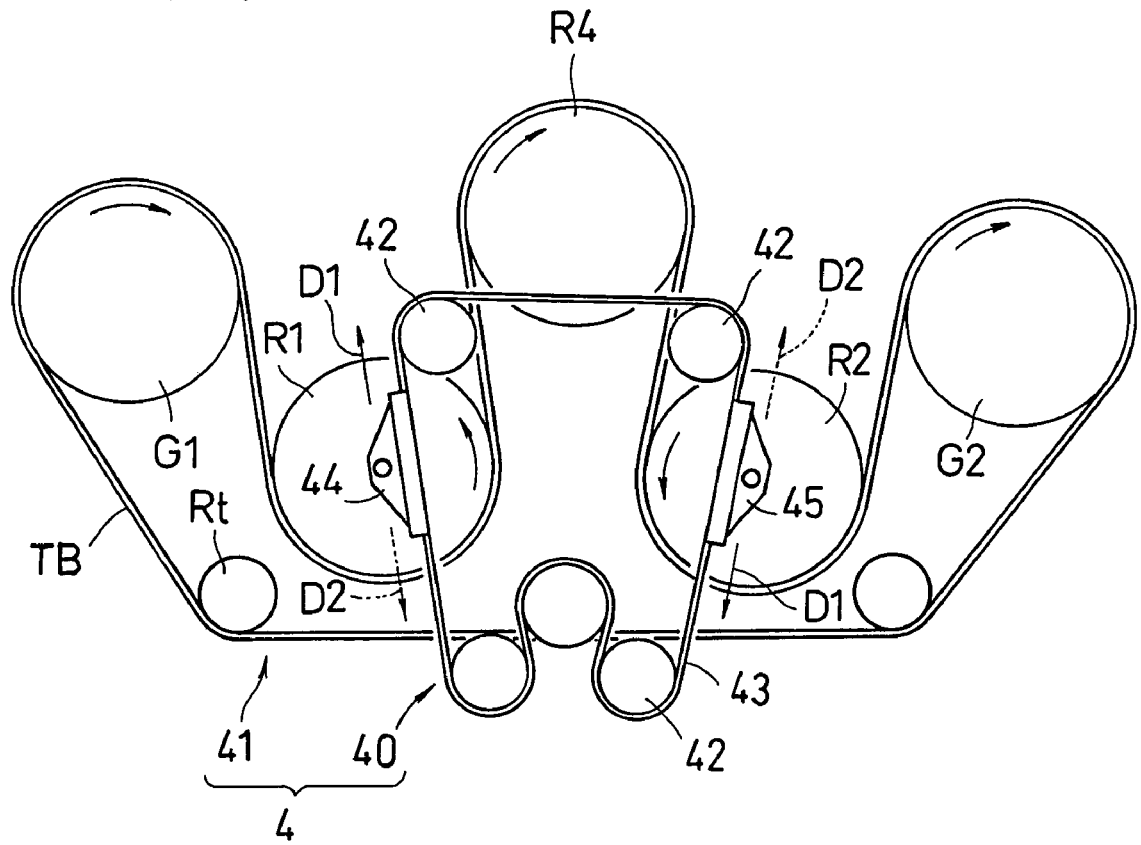
FIG. 2(a) is a schematic side view of a velocity-changing device and FIG. 2(b) is a schematic side view showing another example of an anvil roller.
Figure 2B:
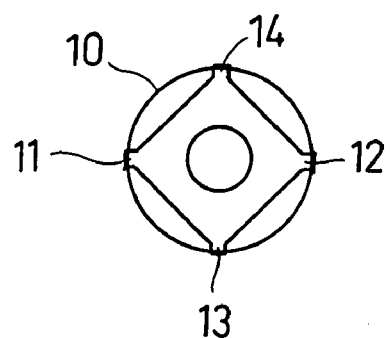
Figure 3:
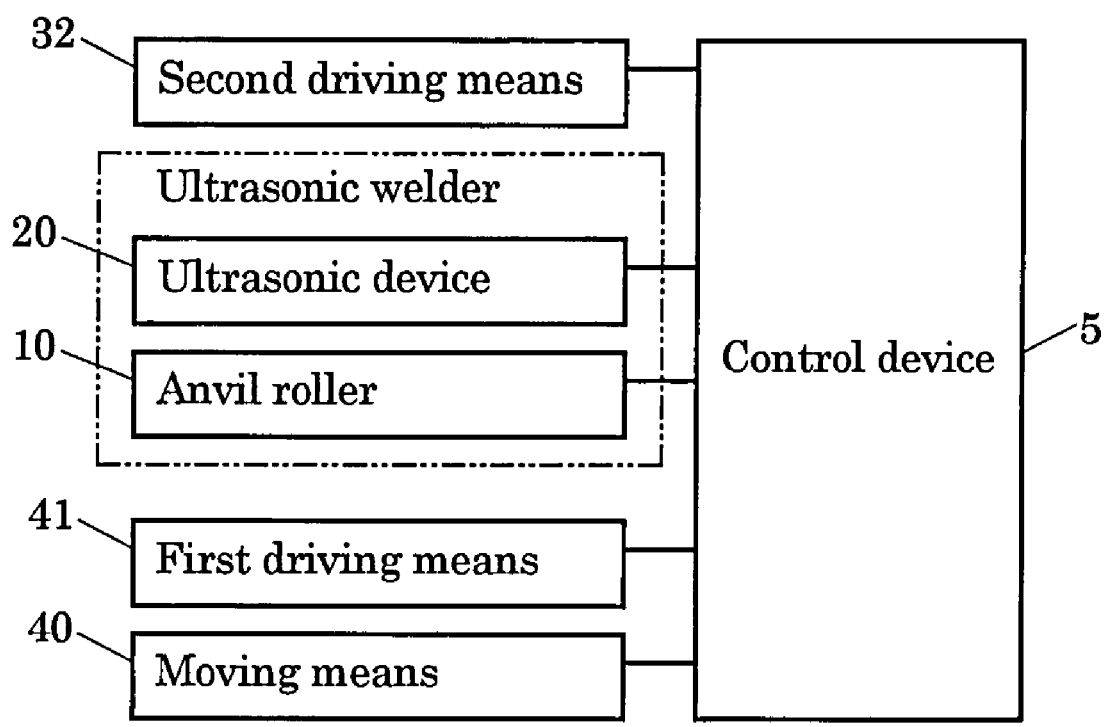
FIG. 3 is a schematic configuration diagram showing an control system.

FIGS. 1 to 3 show the first embodiment.

The present system includes an ultrasonic welding device (ultrasonic welder) for welding together a plurality of webs W, which are stacked on each other, while carrying the webs W. The ultrasonic welder includes: an anvil roller 10 including a pair of anvils 11, 12; a first ultrasonic horn 21 and a second ultrasonic horn 22 that apply vibration energy to the webs W in cooperation with the pair of anvils 11, 12; a pair of ultrasonic devices 20, 20 that generates ultrasonic vibration in the ultrasonic horns 21, 22, respectively.

High frequency mechanical vibrations is transmitted to the ultrasonic horns 21, 22 so that the webs W passing between the ultrasonic horn 21, 22 and the anvil 11, 12 are welded (fusion-bonded) with each other due to frictional heat.

As the ultrasonic horns 21, 22, for example, the ultrasonic horn disclosed in Japanese National Phase PCT Laid-Open Publication No. 10-513128 may be used. The surfaces of the ultrasonic horns 21, 22 may be embossed with a seal pattern having many protrusions. Alternatively, the surfaces of the anvils 11, 12 may be embossed with a seal pattern instead of embossing the surfaces of the ultrasonic horns 21, 22.

Figure 4A:
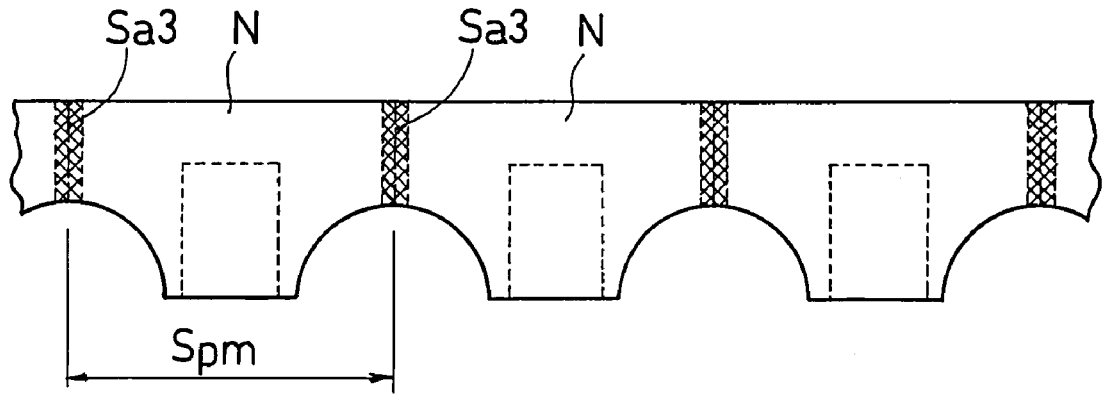
FIGS. 4(a) to 4(c) are a schematic elevation views each showing an example of worn articles before separating each other.
Figure 4B:
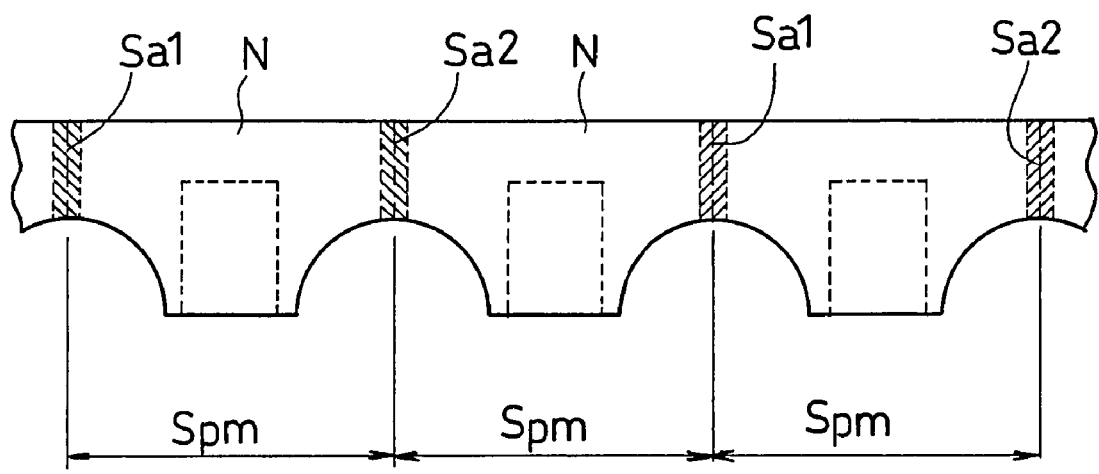
Figure 4C:
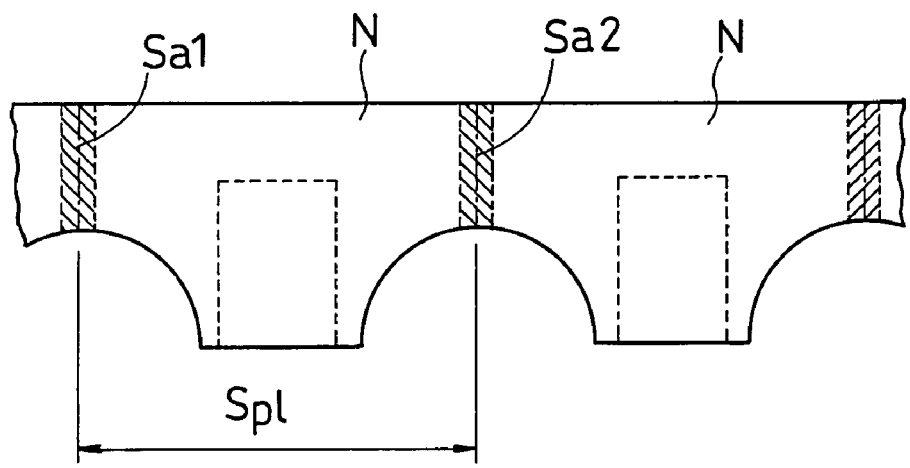

The webs W are formed by stacking a plurality of thermoplastic resin webs that have to be welded with each other. Welded areas Sa1, Sa2, Sa3 of the webs W, which areas are sealed by the ultrasonic devices 20, 20, constitute end portions of individual disposable pants (an example of the worn article), as shown in FIGS. 4(a) to 4(c). The pitch (interval) of the welded areas Sa1, Sa2, Sa3 is set to a predetermined length Spm, Spl, in advance.

The pair of anvils 11, 12 are provided symmetrically with each other with respect to an axis line of the anvils roller 10, i.e., a line that extends along the center O of rotation of the anvils 11, 12. That is, the pair of anvils 11, 12 are provided on the anvil roller 10 at an angular pitch of 180 degrees.

The first and second ultrasonic horns 21, 22 are positioned symmetrically with each other with respect to the center of rotation of the anvils 11, 12. That is, the pair of ultrasonic horns 21, 22 are arranged so that one of the pair of anvils 11, 12 can the first ultrasonic horn 21 simultaneously with the other of the pair of anvils 11, 12 facing the second ultrasonic horn 22.

The pair of ultrasonic horns 21, 22 apply the vibration energy onto the webs W simultaneously in a state where one of the pair of anvils 11, 12 faces the first ultrasonic horn 21 and where the other of anvils 11, 12 faces the first ultrasonic horn 22. Thus, the welding of the webs W is performed at two locations simultaneously. At the time of this welding, the anvil roller 10 receives two forces of opposite directions toward the center 0 of the anvil roller 10, simultaneously, via the webs W, from the ultrasonic horns 21, 22, respectively. Since the anvil roller 10 receives simultaneously the two forces that are in opposite directions to each other, the anvil roller 10 comes to less readily displace even when the ultrasonic horns 21, 22 applies large vibration energy to the anvil roller 10.

As shown in FIG. 2(b), another pair of anvils 13, 14, or another plural pairs of anvils, may be provided on the anvil roller 10, in addition to the pair of anvils 11, 12.

The present system includes a transport apparatus 3 (carrying means for carrying the webs W). This transport apparatus 3 carries the webs W so that the webs W pass a first gap 1 between the anvil roller 10 and the first ultrasonic horn 21 and then pass a second gap 2 between the anvil roller 10 and the second ultrasonic horn 22. The transport apparatus includes an adjustment roller R3, a velocity-changing device 4, which will be described in detail later, and so on. The webs W having passed the first gap 1 flow along an outer circumferential surface of the adjustment roller R3, and then is carried into the second gap. Note that the ultrasonic device 20, 20, the transport apparatus 3 and the like, are arranged so that the upstream side and the downstream side thereof are in mirror symmetry with each other.

The adjustment roller R3 is rotatably supported by supporting means 31. The supporting means 31 rotatably support the adjustment roller R3 selectively at a first position P1 or a second position P2, which positions are different from each other.

In a case where a worn article of the first size (for example, medium size) shown in FIG. 4(a) is to be produced, the adjustment roller R3 is supported at the first position P1 shown by solid line in FIG. 1, by the supporting means 31. On the other hand, in a case where a worn article of the second size (for example, large size) shown in FIG. 4(c) is to be produced, the adjustment roller R3 is supported at the second position P2 shown by one-dot chain line in FIG. 1, by the supporting means 31.

The welded areas Sa1, Sa2, Sa3 of the worn article N shown in FIGS. 4(a) to 4(c) are formed by welding a portion of the webs W at the first gap 1 and the second gap 2 while the webs W go through the gaps 1, 2. The welding at the first gap 1 and the welding at the second gap 2 are performed simultaneously. Accordingly, the length of a portion of the webs W between the first gap 1 and the second gap 2 need to be set to an integral multiple of the pitch (product length) Spm, Spl of the worn article N. By supporting the adjustment roller R3 shown in FIG. 1 selectively at the first position P1 or the second position P2 with the web length kept as above mentioned, worn articles of more than two different sizes can be produced in one system.

The structure of the supporting means is not limited to any specific structure, but the supporting means 31 may have, for example, a structure wherein the center O3 of rotation of the adjustment roller R3 is fixed to a pivot arm which is lockable at two different angular positions. Alternatively, the supporting means 31 may have a structure wherein a bearing supporting the adjustment roller R3 can be fixed selectively among two or more different positions. The supporting means 31 may have a structure wherein worn articles of three or more sizes can be produced.

The velocity-changing device 4 includes the first dancer roller R1, the second dancer roller R2, moving means 40 (FIG. 2(a)) and the first driving means 41. The first dancer roller R1 (FIG. 1) receives the webs W flowing from the upstream side and releases the webs W toward the first gap 1. The second dancer roller R2 receives the webs W flowing from the second gap 2 and releases the webs W toward the downstream side.

The moving means 40 (FIG. 2) reciprocates (swings) the first and second dancer rollers R1, R2, as shown by two-dot line and solid line in FIG. 1. The first driving means 41 rotates the first and second dancer rollers R1, R2 at the same rotational velocity (circumferential velocity).

The first guide roller G1 is rotatably provided on the upstream side of the first dancer roller R1. The second guide roller G2 is rotatably provided on the downstream side of the second dancer roller R2. The first guide roller G1 guides the webs W flowing toward the first dancer roller R1. The second guide roller G2 guides the webs W flowing out of the second dancer roller R2. Between and above the dancer rollers R1, R2, the first drive roller R4 is located. As shown in FIG. 2(a), a timing belt TB is trained around the above mentioned five rollers R1, R2, G1, G2, R4 and a tension roller Rt, etc. Accordingly, this timing belt TB enables the five rollers R1, R2, G1, G2, R4 to rotate in synchronism when the drive roller R4 is rotatably driven.

The velocity-changing device 4 alternates between transport of the webs W at a high moving velocity and transport of the webs W at a low moving velocity, repeatedly. In the transport of the webs W at the high moving velocity, the moving velocity of the webs W between the dancer rollers R1, R2 is larger than the velocity V of the web W flowing into the first dancer roller R1. On the other hand, in the transport of the webs W at the low moving velocity, the moving velocity of the webs W between the dancer rollers R1, R2 is smaller than the velocity V.

That is, in the transport at the high moving velocity, the webs W is transported at the high moving velocity between the dancer rollers R1, R2, by moving both of the dancer rollers R1, R2 so that, as shown by solid line arrow D1 in FIG. 1, the first dancer roller R1 gets close to the anvil roller 10 and, at the same time, the second dancer roller R2 gets away from the anvil roller 10. On the other hand, in the transport at the low moving velocity, the webs W is transported at the low moving velocity between the dancer rollers R1, R2, by moving both of the dancer rollers R1, R2 so that, as shown by broken line arrow D2 in FIG. 1, the first dancer roller R1 gets away from the anvil roller 10 and, at the same time, the second dancer roller R2 gets close to the anvil roller 10.

When the first and second anvils 11, 12 faces a portion of the anvil roller 10 other than the first and second ultrasonic horns 21, 22, the moving velocity of the webs W between the first and second dancer rollers R1, R2 is controlled to be larger than the moving velocity of the webs W flowing into the first dancer roller R1.

On the other hand, when the anvils 11, 12 faces the first and second ultrasonic horns 21, 22, respectively, the moving velocity of the webs W between the first and second dancer rollers R1, R2 is controlled to be smaller than the moving velocity V of the webs W flowing into the first dancer roller R1 and at this time the ultrasonic welding of the webs W is performed.

Thus, when the horns 21, 22 apply the vibration energy onto the webs W, the moving velocity of the webs W passing between the horns 21, 22 and the anvils 11, 12 is set low. In consequence, the webs W can have more time to receive the vibration energy and so the quantity of the received vibration energy per unit area of the webs is increased. Accordingly, the reliability of the welding can be enhanced.

Furthermore, since the pair of anvils 11, 12 and the pair of horns 21, 22 are provided in this system, the number of times the servo motor changes its rotational velocity is halved as compared to a case where only one anvil and one horn are provided. Accordingly, the load on each servo motor periodically changing its rotational velocity can be reduced. In addition, the number of times the dancer rollers R1, R2 are swung per one product can be halved as compared to a case where only one anvil and one horn are provided. Accordingly, the burden on the device or apparatus is reduced, thereby lengthening its useful life.

Since the first driving means 41 of the velocity-changing device 4 of FIG. 2(a) makes the pair of dancer rollers R1, R2 rotate at the same rotational velocity and at a circumferential velocity which is equal to the moving velocity of the webs W, the tension of the webs W between the pair of dancer rollers R1, R2 remains unchanged. In addition, if the two dancer rollers R1, R2 moves at the same moving velocity, the length of the webs W between the two dancer rollers R1, R2 can be kept constant. Thus, the webs W are unlikely to expand or contract.

Now, an arrangement of the dancer rollers R1, R2 will be described.

As shown by solid line in FIG. 1, when the dancer rollers R1, R2 are positioned at the center of the movement, the distance between the first dancer roller R1 and the anvil roller 10 is substantially equal to the distance between the second dancer roller R2 and the anvil roller 10. The dancer rollers R1, R2 are arranged in such a way that the distance between a releasing position of the first dancer roller R1 where the webs W are released from the first dancer roller R1 and a receiving position of the second dancer roller R2 where the second roller R2 receives the webs W is set substantially equal to or smaller than the diameter of the anvil roller 10, when the dancer rollers R1, R2 are positioned at the center of the movement. As a result, compact structure of the velocity-changing device 4 can be realized.

Now, an example of the moving means 40 will be described with reference to FIG. 2(a).

In this moving means 40, a belt 43 for swinging the dancer rollers R1, R2 is trained around, for example, five pulleys 42. The first and second dancer rollers R1, R2 are rotatably attached to the belt 43 by the first and second attachments 44, 45, respectively. This moving means 40 includes two groups of the five pulleys 42 and the belt 43, and the groups are placed beside the dancer rollers R1, R2 on opposite sides of the web flowing direction.

One of the five pulleys 42 is a drive pulley. This drive pulley is rotated in forward and reverse directions by a servo motor (not shown). The rotation of the servo motor in the forward direction makes the belt 43 move in the first direction D1 of solid line arrow, and, as a result, the first and second dancer rollers R1, R2 move in the first direction D1. On the other hand, The rotation of the servo motor in the reverse direction makes the belt 43 move in the second direction D2 of broken line arrow, and, as a result, the first and second dancer rollers R1, R2 move in the second direction D2.

Both dancer rollers R1, R2 repeated reciprocating motion (swinging motion) in the directions D1, D2, thereby that the transport of the webs W at the high moving velocity and the transport of the webs W at the low moving velocity are performed alternately and repeatedly, as above mentioned.

Now, the control of the present system will be described.

As shown in FIG. 3, in this system, the control device 5 controls the ultrasonic devices 20 of the ultrasonic welder and the servo motors of the anvil roller 10, the first driving means 41, the second driving means 32 and the moving means 40. The second driving means 32 rotatably drives the adjustment roller R2 (FIG. 1) via the servo motor.

The control device 5 controls the ultrasonic device 20 and the servo motor of the anvil roller 10 so as to build the following relationship between the timing of actuating the ultrasonic device 20 and the positions of the anvils 11, 12 of the anvil roller 10.

The angular velocity of the anvil roller 10 is controlled so that, according to the size (medium size or large size) of the worn article N shown in FIG. 4(a) and FIG. 4(c), i.e., according to the pitch of the welded areas Sa1, Sa2, Sa3, one of the pair of anvils 11, 12 can face the first ultrasonic horn 21 at the first gap 1 (FIG. 1) at the same time as the other of the pair of anvils 11, 12 faces the second ultrasonic horn 22 at the second gap 2.

The ultrasonic device 20 is controlled so that the first and second ultrasonic horns 21, 22 apply the vibration energy onto the webs W when each of the pair of anvils 11, 12 faces the first ultrasonic horn 21 or the second ultrasonic horn 22, thereby to perform the welding of the webs W. On the other hand, during the time the ultrasonic welding of the webs W is not performed, the ultrasonic device 20 is controlled so that the first and second ultrasonic horns 21, 22 do not apply the vibration energy to the webs W.

The first drive roller R4 is in contact with the webs W being carried from the first dancer roller R1 toward the first gap 1 and in contact with the webs W being carried from the second gap 2 toward the second dancer roller R2. Since the timing belt TB (FIG. 2(a)) is trained about the first dancer roller R1, the second dancer roller R2 and the first drive roller R4, the rotational velocities of the first drive roller R4 and the dancer rollers R1, R2 are changed in synchronism. Accordingly, by controlling the change of the circumferential velocity of the first drive motor R4, the circumferential velocity of the first dancer roller R1 at the releasing point and the circumferential velocity of the second dancer roller R2 at the receiving point are changed in synchronism according to a predetermined velocity curve.

Furthermore, the circumferential velocity of the first drive roller R4 and the circumferential velocity of the adjustment roller R3 are changed in synchronism so that both circumferential velocities are kept the same. The circumferential velocity of the anvil roller 10 and the circumferential velocity of the first drive roller R4 are periodically changed so that both circumferential velocities are the same when the ultrasonic welding of the webs W is performed. Thus, the moving means 40, the first and second driving means 41, 32 and the anvil roller 10 (FIG. 3) are controlled, according to the movement of the dancer rollers R1, R2, so that the circumferential velocity of the first drive roller R4 and the circumferential velocity of the adjustment roller R3 are kept equal to each other and that the circumferential velocity of the anvil roller 10 and the moving velocity of the webs W between the first and second dancer rollers R1, R2 are equal to each other when the ultrasonic welding of the webs W is performed.

Now, the operation of the present system will be described.

As shown in FIG. 1, the webs W flow from the first guide roller G1 to the first dancer roller R1 at a generally constant velocity V and then flow along the outer circumferential surface of the first dancer roller R1. The webs W having exited from the first dancer roller R1 pass the first and second gaps 1, 2 and then flow along the outer circumferential surface of the second dancer roller R2. Subsequently, the webs W are carried toward the second guide roller G2 at a generally constant velocity V.

When the ultrasonic welding is performed, the first dancer roller R1 moves in the direction of arrow D2 so that the length of the webs W between the first dancer roller R1 and the first gap 1 increases, and, at the same time, the second dancer roller R2 moves in the direction of arrow D2 so that the length of the webs W between the first dancer roller R2 and the second gap 2 decreases. By such a movement of rollers R1, R2, the moving velocity of the webs W becomes smaller than the velocity V of the webs W entering into the first dancer roller R1.

When the webs W is carried at the low velocity, the anvils 11, 12 of the anvil roller 10 face the ultrasonic horns 21, 22. At this time, the ultrasonic device 20 is actuated, and, as a result, the adjacent welded areas Sa3, Sa3 (FIG. 4(a)) of the webs W are welded (sealed) simultaneously.

When the ultrasonic welding is not performed, the first dancer roller R1 moves in the direction of arrow D1 so that the length of the webs W between the first dancer roller R1 and the first gap 1 decreases, and, at the same time, the second dancer roller R2 moves in the direction of arrow D1 so that the length of the webs W between the first dancer roller R2 and the second gap 2 increases. By such a movement of rollers R1, R2, the moving velocity of the webs W becomes larger than the velocity V of the webs W entering into the first dancer roller R1.

Regarding the ultrasonic welding, one welded area Sa3 may be welded by both ultrasonic horns 21, 22, as shown in FIG. 4(a). That is, the first ultrasonic horn 21 apply the vibration energy to a portion of the webs W (welded portion Sa3 in FIG. 4(a)) when either of the pair of anvils 11, 12 faces the first ultrasonic horn 21, and then, the second ultrasonic horn 22 apply the vibration energy once again to the portion of the webs W (the welded area Sa3), to which the first ultrasonic horn 21 has applied the vibration energy, when either of the pair of anvils 11, 12 faces the second ultrasonic horn 22. The welded area Sa3 becomes an end portion of the product such as a worn article.

In this case, the moving velocity of the webs W and the angular velocity of the anvil roller 10 are controlled so that the welded area Sa3, which has been welded by the first ultrasonic horn 21 at the first gap 1, is subsequently welded by the second ultrasonic horn 22.

In such a welding, since the vibration energy is applied twice to one portion of the webs W, the reliability of the welding can be enhanced.

On the other hand, as shown in FIG. 4(b), each welded area Sa1, Sa2 may be welded only by either of the ultrasonic horns 21, 22. That is, when either of the pair of anvils 11, 12 faces the first ultrasonic horn 21, the first ultrasonic horn 21 applies the vibration energy to a portion (welded area Sa1 in FIG. 4(b)) of the webs W, and the vibration energy by the second ultrasonic horn 22 is not to be applied to the portion (the welded area) of the webs W to which the first ultrasonic horn 21 has applied the vibration energy. When either of the pair of anvils 11, 12 faces the second ultrasonic horn 22, the second ultrasonic horn 22 applies the vibration energy to another portion (welded area Sa2 in FIG. 4(b)) of the webs W where the vibration energy is not applied by the first ultrasonic horn 21.

In this case, as shown in FIG. 4(b), the welded area Sa1 welded by the first ultrasonic horn 21 and the welded area Sa2 welded by the second ultrasonic horn 22 emerge alternately on the webs W. The pitch between the welded areas Sa1, Sa2 is the length Spm, and therefore, the pitch of the welded areas Sa1, Sa1 welded by the first ultrasonic horn 21 and the pitch of the welded areas Sa2, Sa2 welded by the second ultrasonic horn 22 are the double of the length Spm, respectively. These welded areas Sa1, Sa2 become end portions of the product such as a worn article. In this case, the moving velocity of the webs W and the angular velocity of the anvil roller 10 are controlled so that, after welded areas Sa1, Sa2 are welded at the first and second gap 1, 2, respectively, the webs W are carried by the double of Spm, and then, other welded areas Sa1, Sa2 are welded.

In the case of such a welding, positional misalignment of the welding, which misalignment may occur in the case the vibration energy is applied twice to each welded area Sa1, Sa2, is unlikely to occur. Accordingly, in this case, beautiful worn articles can be produced and the percentage of rejects in the production of worn articles decreases, thereby to improve the production efficiency. In addition, since the ultrasonic welding is performed only once per one welded area, the number of times the dancer rollers the dancer rollers are swung can be reduced, thereby to lengthen the useful life of machine.

Figure 5:
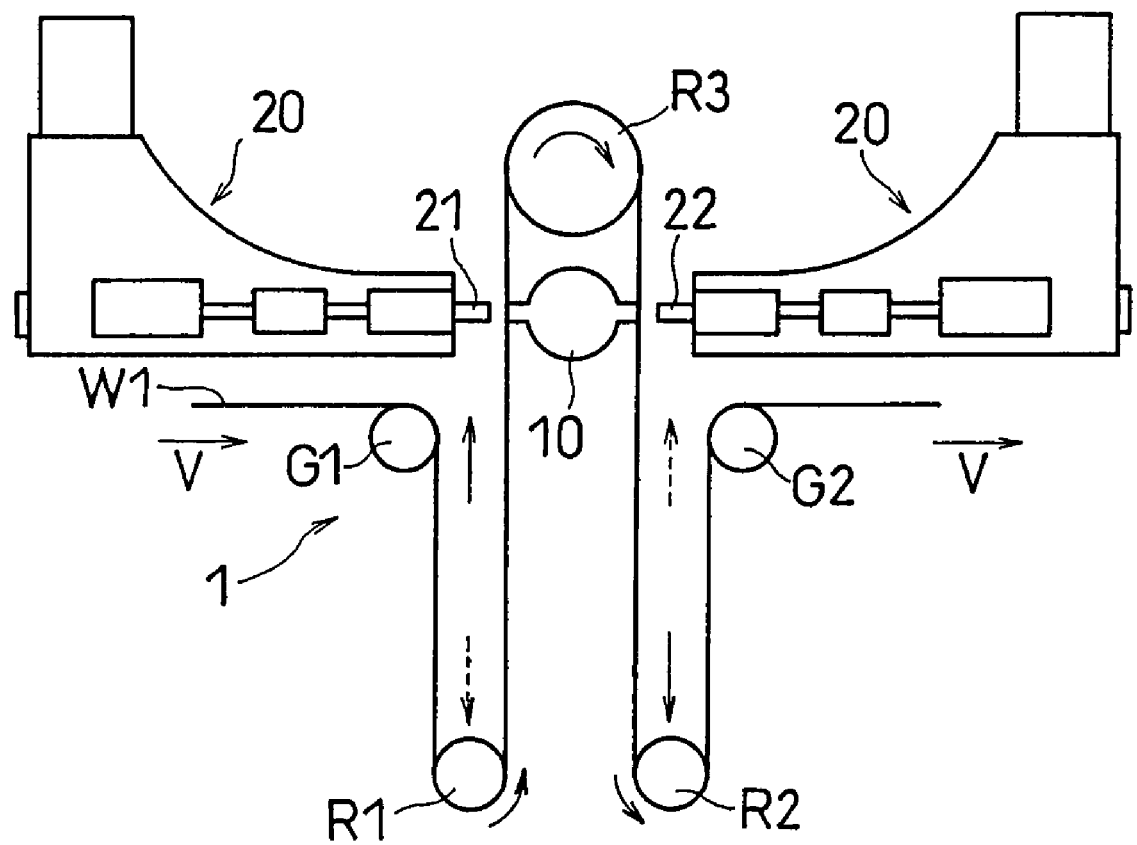
FIG. 5 is a schematic side view showing a welding system of another embodiment.

FIG. 5 shows the second embodiment.

As shown in FIG. 5, the first drive roller R4 which is in contact with the webs W need not necessarily be provided.

Figure 6:
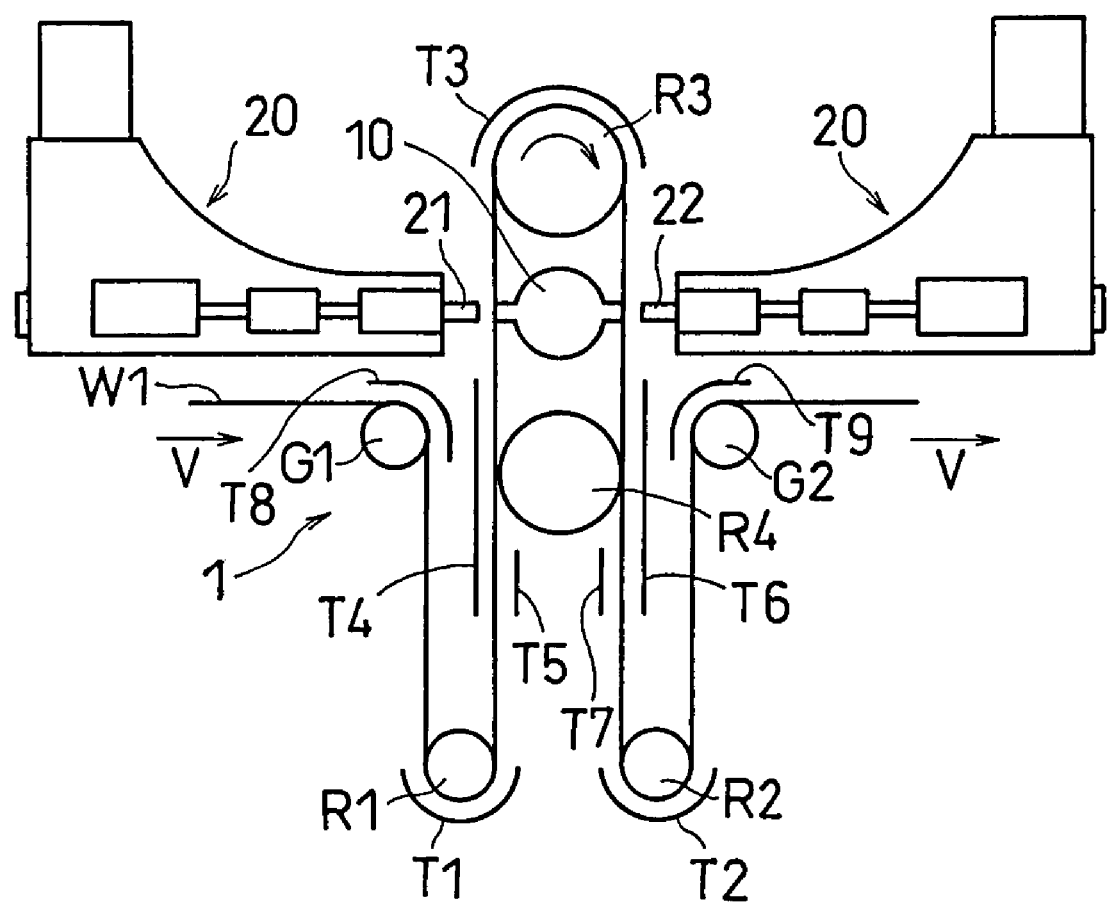
FIG. 6 is a schematic side view showing a welding system of yet another embodiment.

FIG. 6 shows the third embodiment.

As shown in FIG. 6, guides (guide members) T1, T2, T3 for guiding the flow of the webs W may be provided around the three rollers R1, R2, R3, respectively. Similarly, guides T8, T9 for guiding the flow of the webs W may be provided around the first and second guide roller G1, G2. In addition, guides T4, T5 for guiding the flow of the webs W flowing into the first drive roller R4 and guides T6, T7 for guiding the flow of the webs W flowing out of the first drive roller R4 may be provided. These guides T1 to T9 are useful for carrying the webs W smoothly, especially in a case where the weight of the webs W is unbalanced, for example, the webs W is composed of a stack of a plurality of webs including absorbent bodies.

While preferred embodiments of the present invention have been described above with reference to the drawings, obvious variations and modifications will readily occur to those skilled in the art upon reading the present specification.

For example, the adjustment roller and the velocity-changing device need not necessarily be provided.

Fixed roller may be provided instead of the adjustment roller.

The adjustment roller may be supported at the first or second position via means for fine adjusting the position of its shaft center.

In a case where the velocity-changing device is provided, a method for changing the velocity is not limited to the above embodiments.

Other belts or chains may be used instead of the timing belt.

The dancer roller may move right and left instead of moving up and down.

Thus, such variations and modifications shall fall within the scope of the present invention as defined by the appended claims.

INDUSTRIAL APPLICABILITY

The welding system of the present invention is applicable to the production facility for producing disposable worn articles such as disposable pants, disposable diapers and sanitary products and also applicable to the production facility for producing medical wound dressings.

The invention claimed is:

1. A welding system with an ultrasonic welder for welding a plurality of webs together while carrying the webs, wherein the ultrasonic welder comprises:
    an anvil roller including a pair of anvils;
    a first ultrasonic horn and a second ultrasonic horn that apply vibration energy to the webs in cooperation with the pair of anvils; and
    carrying means for carrying the webs so that the webs pass a first gap between the anvil roller and the first ultrasonic horn and then pass a second gap between the anvil roller and the second ultrasonic horn,
    the first and second ultrasonic horns are arranged so that one anvil of the pair can face the first ultrasonic horn at the same time as the other anvil of the pair faces the second ultrasonic horn, and
    the first and second ultrasonic horns apply the vibration energy to the webs simultaneously while each of the anvils faces the first or second ultrasonic horn,
    wherein the pair of anvils are provided symmetrically with each other with respect to an axis line of the anvil roller.

2. A welding system according to claim 1, comprising a velocity-changing device for increasing and decreasing a moving velocity of the webs, wherein
    by the velocity-changing device, the moving velocity of the webs at the first and second gaps when the first and second ultrasonic horns apply the vibration energy to the webs is set smaller than that at a position where the webs enter into the velocity changing device and/or that at a position where the webs exit from the velocity-changing device.

3. A welding system according to claim 2, wherein the velocity-changing device comprises:
    a first dancer roller that receives the webs flowing from an upstream side and releases the webs toward the first gap;
    a second dancer roller that receives the webs flowing from the second gap and releases the webs toward a downstream side; and
    moving means for moving the first and second dancer rollers, wherein
    the moving means can move the first roller and the second roller in generally opposite directions with each other so that the moving velocity of the webs is increased and decreased.

4. A welding system according to claim 2, wherein the velocity-changing device comprises:
    a first dancer roller that receives the webs flowing from an upstream side and releases the webs toward the first gap;
    a second dancer roller that receives the webs released from the second gap and releases the webs toward a downstream side;
    moving means for moving the first and second dancer rollers; and
    a first driving means for rotatably driving the first and second dancer rollers.

5. A welding system according to claim 4, wherein a distance between the first and second dancer rollers is substantially equal to or smaller than a diameter of the anvil roller.

6. A welding system according to claim 4, further comprising a timing belt trained around a plurality of rollers including the first and second dancer rollers and a drive roller, for rotating the plurality of rollers in synchronism.

7. A welding system according to claim 6, further comprising:
    a drive roller which the timing belt is trained about, the drive roller rotatably driven by the first driving means;
    a second driving means for rotatably driving the adjustment roller; and
    a control device that controls the moving means, the first driving means and the second driving means so that both of a circumferential velocity of the adjustment roller and a circumferential velocity of the drive roller are equal to the moving velocity of the webs between the first and second dancer rollers.

8. A welding system according to claim 1, wherein
    when each anvil of the pair faces the first ultrasonic horn or the second ultrasonic horn, the first and second ultrasonic horns are controlled to apply the vibration energy to the webs so that ultrasonic welding of the webs is performed, and
    when the ultrasonic welding of the webs is not performed, the first and second ultrasonic horns are controlled not to apply the vibration energy to the webs.

9. A welding system according to claim 1, wherein
    the carrying means comprises: a adjustment roller that is rotatably supported; supporting means for rotatably supporting the adjustment roller selectively at a first position or a second position that is different from the first position, and
    the webs having passed the first gap flow along an outer circumferential surface of the adjustment roller, and then are carried into the second gap, wherein
    when a semi-finished product including the webs is to be processed into a worn article of a first size, the adjustment roller is supported at the first position by the supporting means, and
    when the semi-finished product including the webs is to be processed into a worn article of a second size that is different from the first size, the adjustment roller is supported at the second position by the supporting means.

10. A welding system according to claim 9, wherein an angular velocity of the anvil roller can be controlled so that, according to the size of the worn article to be produced, one anvil of the pair can face the first ultrasonic horn at the first gap at the same time as the other anvil of the pair faces the second ultrasonic horn at the second position.

11. A welding system according to claim 1, wherein
    when either anvil of the pair faces the first ultrasonic horn, the first ultrasonic horn applies the vibration energy to a portion of the webs, and
    when either anvil of the pair faces the second ultrasonic horn, the second ultrasonic horn applies the vibration energy once again to the portion of the webs where the vibration energy has been applied by the first ultrasonic horn.

12. A welding system according to claim 1, wherein
    when either anvil of the pair faces the first ultrasonic horn, the first ultrasonic horn applies the vibration energy to a portion of the webs, to which portion the vibration energy by the second ultrasonic horn is not to be applied, and
    when either anvil of the pair faces the second ultrasonic horn, the second ultrasonic horn applies the vibration energy to another portion of the webs where the vibration energy by the first ultrasonic horn is not applied.

* * * * *